US008603516B2

(12) United States Patent
Dam et al.

(10) Patent No.: US 8,603,516 B2
(45) Date of Patent: *Dec. 10, 2013

(54) BUCCAL DRUG DELIVERY

(71) Applicants: Anders Dam, Hoersholm (DK); Janos Major, Hoersholm (DK); Peter Tasko, Stevenage (GB)

(72) Inventors: Anders Dam, Hoersholm (DK); Janos Major, Hoersholm (DK); Peter Tasko, Stevenage (GB)

(73) Assignee: Gelmedic Holding APS, Holte (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/685,080

(22) Filed: Nov. 26, 2012

(65) Prior Publication Data

US 2013/0085165 A1 Apr. 4, 2013

Related U.S. Application Data

(63) Continuation of application No. 10/570,697, filed as application No. PCT/GB2004/003811 on Sep. 6, 2004, now Pat. No. 8,343,532.

(30) Foreign Application Priority Data

Sep. 5, 2003 (GB) .................................. 0320854.3
Feb. 16, 2004 (GB) .................................. 0403373.4

(51) Int. Cl.
*A61K 9/68* (2006.01)
*A61K 9/00* (2006.01)
*A61K 9/20* (2006.01)

(52) U.S. Cl.
CPC ............ *A61K 9/0056* (2013.01); *A61K 9/2018* (2013.01)
USPC ........................................................ 424/440

(58) Field of Classification Search
None
See application file for complete search history.

(56) References Cited

U.S. PATENT DOCUMENTS

| | | | |
|---|---|---|---|
| 3,590,117 A | 6/1971 | Christenson et al. | |
| 4,614,654 A | 9/1986 | Ream et al. | |
| 4,829,056 A | 5/1989 | Sugden | |
| 5,047,248 A | 9/1991 | Calanchi et al. | |
| 5,156,845 A | 10/1992 | Grodberg | |
| 5,470,566 A | 11/1995 | Lutzen | |
| 5,549,906 A | 8/1996 | Santus | |
| 5,651,936 A * | 7/1997 | Reed et al. .................. | 420/3 |
| 5,662,920 A | 9/1997 | Santus | |
| 5,762,961 A | 6/1998 | Roser et al. | |
| 5,939,091 A | 8/1999 | Eoga et al. | |
| 6,083,531 A | 7/2000 | Humbert-Droz et al. | |
| 6,110,495 A * | 8/2000 | Dam .................. | 424/464 |
| 6,183,775 B1 * | 2/2001 | Ventouras .................... | 424/465 |
| 6,264,981 B1 * | 7/2001 | Zhang et al. .................. | 424/451 |
| 6,280,761 B1 | 8/2001 | Santus | |
| 6,458,400 B1 | 10/2002 | Willibald-Ettle et al. | |
| 6,548,082 B1 | 4/2003 | Rubin et al. | |
| 6,552,024 B1 | 4/2003 | Chen et al. | |
| 2002/0012675 A1 | 1/2002 | Jain et al. | |
| 2003/0185884 A1 | 10/2003 | Singh et al. | |
| 2003/0229027 A1 | 12/2003 | Eissens et al. | |
| 2004/0052851 A1 | 3/2004 | Graff et al. | |
| 2004/0101543 A1 | 5/2004 | Liu et al. | |

FOREIGN PATENT DOCUMENTS

| | | | |
|---|---|---|---|
| EP | 0500658 | 1/1994 | |
| EP | 1666030 | 6/2006 | |
| EP | 1938806 | * 2/2008 | ............... A61K 9/22 |
| GB | 2049417 | 12/1980 | |
| JP | 63-503225 | 11/1988 | |
| JP | 5-501880 | 4/1993 | |
| JP | 2000-503543 | 3/2000 | |
| JP | 2000-504028 | 4/2000 | |
| JP | 2000-505429 | 5/2000 | |
| JP | 2000-508649 | 7/2000 | |
| JP | 2006-503046 | 1/2006 | |
| WO | 8705212 | 9/1987 | |
| WO | 9106288 | 5/1991 | |
| WO | 9503050 | 2/1995 | |
| WO | 9517829 | 7/1995 | |
| WO | 9600070 | 1/1996 | |
| WO | 9728789 | 8/1997 | |
| WO | 9730598 | 8/1997 | |
| WO | 9738679 | 10/1997 | |
| WO | 9742941 | 11/1997 | |
| WO | 0137814 | 5/2001 | |
| WO | 02076211 | 10/2002 | |
| WO | 02085119 | 10/2002 | |
| WO | 03039518 | 5/2003 | |
| WO | 2004024124 | 3/2004 | |

OTHER PUBLICATIONS

"X-Ray Diffraction," Handbook of Instrumental Techniques for Analytical Chemistry, 1997, pp. 339-361.
Lees, R., "General Technical Aspects of Industrial Sugar Confectionery Manufacture," Sugar Confectionery Manufacture by E.B. Jackson, pp. 106-128, 2013.
Jackson, E.B. et al., "Gluclose Syrups and Starch Hydrolysates," Sugar Confectionery Manufacture, pp. 13-36, 2013.
Stansell, D.I. "The Compositions and Structure of Confectionery," Composition and Structure, pp. 289-311, 2013.
Beacham, J., "Tablets, Lozenges and Sugar Panning," Sugar Confectionery Manufacture, pp. 236-257, 2013.

* cited by examiner

*Primary Examiner* — Brian Gulledge
(74) *Attorney, Agent, or Firm* — Florek & Endres PLLC

(57) ABSTRACT

A lozenge is provided that has stable pH and stable levels of active ingredient over time. It comprises a combination of (i) at least one gum and (ii) at least one non-crystallising sugar or non-crystallising sugar alcohol in a matrix designed for controlled buccal delivery of a drug. The lozenge also contains water and optional components selected from flavorings, taste masking agents, colorings, buffer components, pH adjusting agents, excipients, stabilizers and sweeteners. Methods of preparing the lozenge are also provided.

39 Claims, No Drawings

BUCCAL DRUG DELIVERY

The present invention relates to lozenges for buccal drug delivery and methods for making lozenges for buccal drug delivery.

A known form of buccal drug delivery uses fast melt technology, which is characterised by rapid drug release. A known fast melt product is Zydis, which is formulated as a wafer having a very low density and minimal quantities of excipient. Thus, for example U.S. Pat. No. 5,939,091 describes a method of making fast melt tablets comprising Sorbitol Instant. Similarly, WO 02/085119 describes a dosage form for intra-oral delivery of nicotine comprising a hydroxypropylmethylcellulose film. This delivery system is characterised by rapid dissolution providing for almost instantaneous delivery of the nicotine.

In other forms, the structure of the tablet is modified so as to provide a desired delivery profile. Thus, WO 03/039518 describes an oral dosage formulation for delivery of nicotine comprising two layers, the first providing for buccal drug delivery and the second providing for delivery via the stomach or intestines. This formulation provides an initial rapid release of nicotine in the mouth followed by a slow sustained release of nicotine in the gut.

Also in this category is WO 01/37814 which describes bilayered buccal tablets comprising nicotine. These tablets provide a biphasic release of nicotine from a modified lactose and magnesium stearate containing tablet.

Some known formulations for administering nicotine contain a gum. For example, WO 02/076211 describes an oral dosage formulation comprising nicotine. A formulation is described which is a hard lozenge having a matrix which is in a glassy, i.e. amorphous physical state. These lozenges are made and deposited at high temperatures (for example 120° C.) and comprise a sodium carbonate buffer.

Others include EP 0 500 658, which describes a nicotine containing stimulant unit for buccal drug delivery, which can comprise a gum component and, as a sweetener, a sugar component and U.S. Pat. No. 6,183,775, which describes a controlled release lozenge comprising a soluble filler, an insoluble film-forming agent, and a swellable polymer. The lozenges are produced by compression of a dry granulate.

Other known dosage forms include:
- U.S. Pat. No. 3,590,111, which describes the production of troches by wet and dry granulation procedures. Ingredients include guar gum, disaccharides and hexahydric saturated aliphatic alcohols.
- U.S. Pat. No. 4,829,056, which discloses a buccal tablet containing etorphine as active ingredient and excipients including at least one monosaccharide or disaccharide and locust bean gum.
- U.S. Pat. No. 5,470,566, which discloses an anticariogenic chewing gum comprising a gum base, a taste enhancer and urea for neutralizing dental plaque.
- GB 2 049 417, which discloses an antacid composition compressed into lozenges which can comprises mannitol and xanthan gum.
- U.S. Pat. No. 5,156,845 describes a dry mouth lozenge comprising a non-cariogenic sweetener such as sorbitol, a gum base and a fluoride, and
- WO 96/00070, which discloses a nicotine-containing composition that additionally contains caffeine. Examples of dosage forms include lozenges which contain sugars and adhesive substances including gums.

The known delivery systems tend to produce a rapid release of drug in the mouth or do not provide a controlled rate of release. A further disadvantage of known delivery systems for administering nicotine, is that nicotine may be lost in manufacture or storage due to volatilisation or chemical instability.

Another disadvantage of known hard lozenges containing sodium carbonate is that the sodium carbonate buffer may decompose at the temperatures required for manufacture. Such lozenges may also be subject to variable or over-rapid drug release as they have a mouth feel which is likely to prompt chewing or sucking rather than parking the lozenge and allowing it to dissolve.

Thus there is a need for an improved drug delivery system which is stable and provides controlled buccal delivery of a drug.

According to a first aspect of the present invention, there is provided a glassy lozenge for buccal drug delivery comprising:
 a) a matrix;
 b) an active agent;
 c) water; and
 d) optionally one or more components selected from flavourings, taste masking agents, colourings; buffer components, pH adjusting agents, excipients, stabilizers and sweeteners,
 wherein the matrix comprises (i) at least one gum and (ii) at least one non-crystallising sugar or non-crystallising sugar alcohol.

It is particularly preferred for the matrix of lozenges according to the invention to comprise:
 (i) at least one gum, and
 (ii) at least one sugar and/or at least one sugar alcohol, characterised in that a major proportion of component (ii) consists of:
  A. at least one non-crystallising sugar,
  B. at least one non-crystallising sugar alcohol, or
  C. a mixture of at least one non-crystallising sugar and at least one non-crystallising sugar alcohol.

Preferably such lozenges are characterised in that 50-90 wt %, more preferably 55-85 wt %, and most preferably 60-80 wt % of component (ii) consists of:
 A. at least one non-crystallising sugar,
 B. at least one non-crystallising sugar alcohol, or
 C. a mixture of at least one non-crystallising sugar and at least one non-crystallising sugar alcohol.

Preferably components A, B and C are incorporated into the composition in a pre-existing non-crystallising form.

According to an alternative definition of lozenges according to the invention, it is particularly preferred for the matrix of lozenges according to the invention to comprise:
 (i) at least one gum, and
 (ii-a) at least one sugar and/or at least one sugar alcohol, characterised in that a major proportion of component (ii-a) consists of a non-crystallising mixture of sugars and/or sugar alcohols.

In producing lozenges according to this alternative definition it is not essential that components A, B and C are incorporated into the composition in a pre-existing non-crystallising form.

In other words, the sugar and/or the sugar alcohol in component (ii-a) may initially be in crystalline form. The lozenges of the invention may accordingly be produced by forming a mixture comprising at least one crystallizing sugar and/or at least one crystallizing sugar alcohol, whereby the act of forming the mixture (or subsequent treatment steps performed thereon, such as heating or evaporation of water) results in the mixture as a whole being non-crystallising. Thus in one embodiment, a mixture is formed of (A) non-crystallising sorbitol and (B) a crystalline grade of xylitol, the mixture as a whole being non-crystallising.

As the non-crystallizing sugars and/or sugar alcohols are sweet, it is not necessary for additional sweetening agents (such as sucrose) to be used. In fact, it has surprisingly been found that the advantageous pharmacological properties of the lozenge according to the invention are most pronounced if the lozenges are substantially sucrose-free. By "substantially sucrose-free" is meant that the lozenges containing less than 10 wt % sucrose, preferably less than 5 wt % and most preferably less than 2% sucrose. It is particularly desirable for the lozenges to contain less than 1 wt % sucrose.

Typical glassy lozenges according to the invention comprise the following matrix components in the relative parts by weight specified (excluding water):

| | |
|---|---|
| Acacia gum | 55-62 |
| Sorbitol | 27-34 |
| Xylitol | 7-11 |
| Alkaline metal (e.g. Na) phosphate(s) | 1-13 | especially:

| | |
|---|---|
| Acacia gum | 56-58 |
| Sorbitol | 29-31 |
| Xylitol | 8-10 |
| Alkaline metal (e.g. Na) phosphate(s) | 1.5-2.0 |

Typical water contents of the lozenges are 5-20 wt. %, especially 10-15 wt. %.

Lozenges of the invention have been found to exhibit improved pH stability and stability of the active agent over time and to provide a controlled drug release profile.

According to an embodiment of the invention the lozenge provides for controlled release of the active agent. According to this embodiment, the lozenge dissolves or disintegrates gradually, thus releasing a controlled dose of the drug for absorption across the buccal mucosa. This controlled drug release avoids delivery of an initial burst of drug, and, in some cases, allows the patient to titrate the amount of drug received. Thus, for example, the patient can remove the lozenge from their mouth once the symptoms for which the active agent is administered have been reduced to a tolerable level or eliminated.

The release profile of the active agent or the dissolution profile of the lozenge is governed by the matrix composition and lozenge size and can be varied according to the nature of the active agent and the desired effect. Thus, the dissolution profile can be altered, whilst retaining the same amount of the active agent, by varying the lozenge size and/or the proportion of gum in the lozenge. A smaller overall lozenge size will result in faster dissolution. Similarly a reduced gum content will result in faster lozenge dissolution.

A suitable dissolution profile for lozenges of the invention is such that after 20 minutes approximately 35-65% of the lozenge has dissolved, after 40 minutes, approximately 60-90% of the lozenge has dissolved, and after 60 minutes more than 70% of the lozenge has dissolved. Preferred lozenge sizes are in the region of 300 mg-2 g. Typically lozenges are not smaller than 300-400 mg and are not larger than approximately 1.5 g, approximately 1.75 g or approximately 2 g. In general, lozenge size (in terms of dimensions and shape) should be suitable for parking the lozenge in the buccal cavity.

The ratio of matrix components can be varied to vary the dissolution profile. Typically, the matrix comprises from 40-90% of the gum component and from 60-10% of the non-crystallising sugar or non-crystallising sugar alcohol component. In further embodiments of the invention the matrix comprises 50-80% or preferably 55-75% of the gum component and 20-50% or preferably 25-45% of the non-crystallising sugar or non-crystallising sugar alcohol component.

To calculate the percentage contribution of each component, it must be appreciated that the end lozenge would generally have a moisture content of approximately 5-20% by weight, typically approximately 10-15%. Gum arabic, when used, has a water content of typically about 10%. This should be taken into account unless the proportions of ingredients are defined in terms of the anhydrous equivalent.

Any suitable gum may be used in the lozenges of the invention. Suitable gums include gum acacia, gum arabic, carob gum, carrageenan, ghattii gum, guar gum, karaya gum, pectin, tragacanth gum, locust bean gum and xanthan gum. A preferred gum component is gum acacia, especially supplied in spray dried form for manufacture of lozenges.

In addition to the gum, the matrix also comprises one or more non-crystallising sugars and/or one or more non-crystallising sugar alcohols. Non-crystallising forms of sugars or sugar alcohols are commercially available and may conveniently be used. Alternatively, sugars or sugar alcohols can be heat treated to provide non-crystallising properties. For example, sugars or sugar alcohols may be heated to approximately 110-120° C., preferably 113-117° C., for example, about 114° C. until converted to a non-crystallizing form. Suitable sugars and sugar alcohols for use according to the invention include non-crystallising or treated forms of dextrose, maltose, sucrose, fructose, glucose syrup, invert sugar syrup, honey, laevulose, sorbitol, xylitol, maltitol, mannitol and isomalt. Preferred non-crystallising sugars or non-crystallising sugar alcohols include non-crystallising forms (or mixtures) of sorbitol, xylitol, maltitol, mannitol, and isomalt. According to a particular embodiment of the invention the non-crystallising sugar or non-crystallising sugar alcohol is a non-crystallising form of sorbitol or a mixture of non-crystallising sorbitol with a minor amount, up to 45%, of xylitol. The xylitol is preferably incorporated into the sorbitol/xylitol mixture in non-crystallising form. However, it has been found that if a crystalline grade of xylitol is admixed with non-crystallising sorbitol, a resulting non-crystallising mixture may be obtained. Thus, generally, it is preferred for each lozenge component to be provided in a non-crystallizable form before blending with other components. However if more than one sugar or sugar alcohol is used, the non-crystallizing nature of component (iii) in its totality may derive from the fact that a mixture is used, irrespective of the fact that one of the plurality of sugars/sugar alcohols was initially provided in crystalline form.

The non-crystalline nature of the matrix yields a glassy, amorphous lozenge, which is generally translucent and flexible. Lozenges prepared in specific embodiments of the invention, described in more detail in the examples, demonstrated long-term active agent stability. The potency and/or integrity of the active agent in lozenges of the invention has been found to be substantially constant after storage periods of, for example, three, six, nine twelve or eighteen months:

The glassy, non-crystalline nature of the matrix results in a significant reduction in hydrolysis of the active agent and may result in no hydrolysis. Although not being bound by theory, it is believed that the structure of the matrix (e.g. a hydrogel) results in there being less water and fewer free ions (particularly hydroxyl ions) to initiate hydrolysis. Moreover, the active agent is bound in the matrix and little of none is lost via evaporation from the lozenge. In contrast, the active agent is more susceptible to hydrolysis and is more susceptible to evaporation in a crystalline matrix, such as those of known non-gel lozenges. Thus, the lozenges of the invention exhibit improved stability in storage.

The non-crystalline nature of the matrix may also contribute to the long term stability of the water content of lozenges of the invention. Lozenges of the invention have been found to have a substantially unchanged water content after storage for, for example, three, six, nine twelve or eighteen months.

It is believed that the non-crystallising sugars or non-crystallising sugar alcohols, particularly when used in the preferred proportions described herein, contribute to the glassy structure of the lozenges of the invention. Thus, the non-crystallising sugars or non-crystallising sugar alcohols are structural components of the lozenges, not merely sweeteners, and contribute to the improved stability of the lozenges.

The lozenges according to the invention will normally contain water. Thus according to an embodiment of the invention, the lozenges have a final water content of approximately 5-20% by weight. Lozenges according to the invention may comprise, for example, approximately 9-15% by weight water, preferably approximately 10-13% by weight water.

Lozenges according to the invention may further comprise a buffer system comprising buffer components. For example, the buffer system may comprise one or more alkaline metal salts and corresponding weak acids or weak bases. Any suitable physiologically compatible buffer system may be used which provides buffering capacity at the desired lozenge pH. For example, phosphate, citrate, and carbonate buffers may be included, but the preferred buffer for use according to the invention is a phosphate buffer system. The phosphate buffer system may comprise, for example, sodium dihydrogen phosphate and tri-sodium phosphate and details of further phosphate buffers are set out in the examples. Most preferably citrate buffer and carbonate buffers are excluded and the sole buffering agents are phosphate salts.

It is preferred that the buffer system in the lozenge provides, in the mouth, a pH suitable for buccal absorption of the active agent. The buffer can vary according to the active agent, and generally varies so as to provide a pH at which the active agent is in an un-ionized form. For nicotine-containing lozenges, the pH is preferably in the range 7.5-9.0, more preferably 8.0-8.4. The lozenge may also contain a pH adjusting agent suitable for bringing the pH into the desired range. Such pH adjusting agents are generally basic pH adjusting agents, e.g. water soluble alkali salts, though any suitable agent may be used. Examples of suitable pH adjusting agents include sodium hydroxide, potassium hydroxide and the like.

The presence of a buffer in lozenges of the invention (particularly phosphate buffering agents) results in improved long-term stability in the pH value of the lozenges. For example, lozenge pH values may be substantially stable during storage for up to three months, six months, nine months, twelve months, or eighteen months. Use of a phosphate buffer system has been found to be particularly effective in providing long-term stability, in lozenge pH.

Also, the presence of a buffer, particularly a phosphate buffer, has been found to contribute to the long-term stability of the active agent during storage. This may be, in part, due to the maintenance of a stable pH. The active agent in lozenges of the invention may be stable for up to three months, up to six months, up to nine months, up to twelve months, or up to eighteen months. While not being bound by theory, it is believed that a synergistic effect between the preferred phosphate buffer and other components (especially non-crystallizable sorbitol) contributes to the advantages described.

In addition, it may be desirable to have the active agent present in the lozenge in a particular form, such as an un-ionised form. The lozenge pH can be set to a particular value or range of values suitable for a given active agent by varying the nature or amount of the buffering agents and/or pH adjusting agents.

It is believed that control of the lozenge pH, and in particular the use of phosphate buffers is advantageous in providing an improved taste or "mouth feel". The use of phosphate buffers, for example, avoids the presence of the "soapy" taste or texture sometimes associated with other buffers (e.g. carbonates). This may be useful in encouraging reluctant patients to take necessary medication.

Carbonate buffers are not preferred as they tend to decompose at high temperatures, causing bubbles to form in the matrix. Citrate buffers are not preferred for basic buffered lozenges, for example lozenges having nicotine as the active agent, as they do not provide the optimal pH.

Lozenges according to the invention may optionally comprise flavourings, vitamins, anti-oxidants, anti-fungals, anti-bacterials, taste masking agents, colourings, excipients; stabilisers and sweeteners. Suitable components may be selected from those known in the art. Flavourings can include toffee flavouring QL17192, lemon oil, orange oil, and spearmint flavour 79020. Colourings may include any colouring approved for food or pharmaceutical use. Excipients may include talc, maize starch, and Capol 4348F. According to some embodiments of the invention, the excipients form a coating on the surface of the lozenge and are not incorporated into the lozenge itself. Sweeteners may include artificial sweeteners such as aspartame and sodium saccharin, sugars and sugar alcohols as previously listed. It is preferred that sugars or sugar alcohols used as sweeteners be non-crystallising or be treated to impart non-crystallising properties and that sucrose is absent.

According to another aspect of the invention, a lozenge for buccal drug delivery is provided comprising a matrix and a phosphate buffer, wherein the matrix comprises (i) a gum, and (ii) a sugar or sugar alcohol.

In lozenges of this aspect of the invention, the phosphate buffer preferably comprises a pH adjusting agent and one or more phosphate buffer salts. Generally, the buffer and its components are as described for other lozenges of the invention. Further, the remaining components of the lozenge of this aspect are as described in relation to other lozenges of the invention, apart from the matrix. The sugar component of the matrix is not necessarily non-crystallizing, and hence this aspect of the invention relates to use of a phosphate-based buffer system in preparation of a matrix for a buccal lozenge. Use of phosphate-based buffers has been found to confer taste and stability advantages as demonstrated in the examples provided herein.

Generally, and in relation to all lozenges of the invention, the active agent can be selected from any active agent, drug, pharmaceutical or the like that is desired to be delivered buccally, that is to say absorbed across the buccal mucosa.

Drugs particularly suitable for delivery using lozenges of the invention include alkaloids, for example nicotine, alkaloidal drugs, anti-emetics (for example 5-HT antagonists), agents for migraine treatment (for example 5-HT agonists), analgesics (for example *cannabis,* Δ9-THC and alkaloids), drugs that benefit from rapid uptake, drugs used in acute therapy, drugs that need to be or are preferentially taken lying down, drugs taken by patients who cannot or do not wish to swallow or drugs to be taken where it is undesirable to use a large amount of water. Drugs are preferably readily absorbable across the buccal mucosa. Drugs particularly suitable for delivery via lozenges of the invention are drugs for which the first pass effect is not beneficial, ie drugs of which the potency is reduced as a result of metabolism in the liver. Mucosal delivery is ideal for such drugs as they are directly absorbed into the bloodstream without first passing through the liver.

Particularly preferred drugs for delivery using lozenges of the invention include nicotine, the analgesic Δ9-THC, the anti-emetic ondansetron (a $5-HT_3$ antagonist), and the anti-migraine drug sumatriptan (a 5-HT, agonist). Drugs for delivery using lozenges of the invention may optionally be in the form of a pharmaceutically acceptable salt.

For lozenges in which the active agent is nicotine, this may be provided as synthetic nicotine or nicotine extracts from tobacco plants, i.e. the genus *Nicotiana*. The nicotine can be in the form of the free base, pharmaceutically acceptable acid addition salts or oxidation products such as nicotine-1'-N-oxide. Lozenges according to the invention may also comprise alkaloids with the same direction of activity as nicotine including nor-nicotine and lobeline (e.g. of the species *Lobeliaceae* and *Lobelia*), methylanabasine and anabasine.

The drug delivery system of the invention may be used to administer any suitable dose of an active agent. Typical doses may be in the range 0.5-10 mg, but doses of approximately up to 200 mg can be delivered by lozenges of the invention. Typically different doses of a given drug are provided by lozenges having the same size, but with varying drug concentration.

The delivery system provided by the lozenges of the invention is particularly suitable for active agents where it is desirable to limit patient exposure to the agent. The controlled release characteristics of the lozenges allow self-titration of the drug dosage by the patient. This is useful, for example, when the lozenges are used to deliver agents for migraine treatment or analgesics. Once sufficient active agent has been absorbed to overcome the symptoms for which the agent has been administered, the remainder of the lozenge can be removed from the patient's mouth.

According to a second aspect, the invention provides a method of making a lozenge for buccal drug delivery comprising a matrix, an active agent and water comprising the steps:

(a) mixing a gum, at least one non-crystallising sugar or sugar alcohol and water;
(b) adding an active agent and mixing;
(c) moulding the mixture to form lozenges.

The method of the invention preferably includes at least one heating step (d), normally carried out between steps (a) and (b) and a final conditioning step to reduce the water content of the lozenges.

According to a further aspect, the invention provides a method of making a lozenge comprising a matrix, an active agent and water for buccal drug delivery comprising the steps:

a) mixing a gum, one or more non-crystallising sugars or non-crystallising sugar alcohols and water;
b) heating the mixture with mixing;
c) adding an active agent and mixing; and
d) moulding the mixture to form lozenges.

The method includes a step of heating and mixing the combination of the gum and sugar component in water, ensuring a throughly mixed, homogenous mass is obtained. Known methods do not heat and mix these components together and can result in lozenges that have an inconsistent composition across the lozenge, leading to an inconsistent texture or appearance. Lozenges prepared according to the method of the invention have a consistent composition and demonstrate improved appearance and improved stability during storage.

Preferably the mixture is heated in step (b) to at least 90° C., generally approximately 110-120° C., more preferably 113-117° C. This ensures that the components are fully dissolved, ensures the matrix components are in a non-crystallising form, and facilitates preparation of a homogeneous mass.

The methods and components of the invention advantageously allow preparation of the cooked mass and incorporation of the active ingredient at relatively low temperatures: Known methods of preparing sugar-containing lozenges and/or confectionary typically employ temperatures well in excess of 100° C. and often in excess of 130° C. We have found that we can avoid these high temperatures but still generate a matrix having consistent properties and yielding a lozenge which is stable in storage. Methods of the invention employ sufficient water to ensure that the gum and sugar components are fully dissolved at the temperatures used, and the amount of water used in the methods can be higher than used in prior art methods. In consequence, the methods of the invention generally include a step of drying the lozenges after they have been moulded, and the methods generally do not include a step of carrying out mixing and/or heating at such a temperature or under such conditions that water is substantially removed from the mass prior to moulding. Further, once the matrix is prepared the active agent is added to the mass at temperatures sufficiently low to avoid degradation of the active agent due to heat or loss due to volatilisation. Addition of the active agent preferably takes place at a temperature of 100° C. or lower, more preferably of 90° C. or lower and in particular at 80° C. or lower. Subsequent processing steps, such as the moulding step, also take place preferably at 100° C. or lower, more preferably 90° C. or lower and in particular 80° C. or lower. A consequent advantage is that active agent loss or degradation is minimised during preparation of lozenges and during and after moulding. Thus, methods according to the invention provide lozenges having improved uniformity of active agent content between lozenges.

The active agent to be added to the cooked mass may be formulated in various ways, according to the nature of the active agent. For example, the active agent may be added in the form of a micronised powder, an ethanolic solution, or an aqueous solution.

Optionally, the method further comprises the steps of adding one or more buffering agents and adding a pH adjustment agent to adjust the pH to approximately 7.5-9.0. The mixture can be allowed to rest following addition of all components but prior to moulding to allow air to escape from the mass. Use of lower temperatures during processing steps leads to reduced degradation of lozenge components, for example reduced degradation of carbonate-containing components to release carbon dioxide which would form bubbles in the mixture. Both result in improved lozenge composition and appearance.

Typically moulding step (d) above comprises the substeps of (d1) transferring the mixture to a moulding apparatus and (d2) moulding the mixture to form lozenges. After moulding a further step comprising drying the lozenges can be carried out.

Thus, specific lozenges according to the invention can be made, for example, by combining a 70% solution of non-crystallising sorbitol, xylitol and gum acacia, dissolving in water and heating to a temperature of approximately 113-117° C., for example 114° C. Heating may be achieved by direct heat transfer, for example, using a jet heater or by indirect heating using a heat exchange surface. Heating to this temperature endows the xylitol with non-crystalline characteristics.

Following heating, the pipework is chased with additional water, buffering agents and optional flavourings are added to the cooked mass and the pH of the mass is adjusted, for example, with sodium hydroxide.

For nicotine-containing lozenges, the pH of the mass is preferably approximately 0.5-1.5 pH units below the final pH of the lozenge. Preferred pH values for the cooked mass lie in the range of pH 6.9-7.1, and preferred final pH values for the lozenge, after addition of nicotine, are in the range 8.0-8.5. Nicotine is added to the cooked mass dissolved in 70% alcohol or in aqueous solution. Preferably a 10% solution of nicotine in 70% alcohol is used. The mixture is stirred for preferably at least 10 minutes and then allowed to rest for approximately 30 minutes to allow air to escape from the mass before forming. During the resting period the mass is preferably maintained at approximately 70° C.

It is preferred that after nicotine is added to the mass, moulding of the lozenges is not overly delayed. Maintaining the mass at the resting temperature for extended periods of time can result in loss of potency due to volatilisation of nicotine, which has a low vapour pressure.

Lozenges may be moulded using known technology. In such methods mass may be transferred to a hot funnel located above depositing funnels. The mass may then be deposited through nozzles into trays of preformed starch moulds. Preferably the starch moulds are conditioned by running through the moulding process several times, for example 7-8 times or 10 times. This conditioning provides repeated compression and heating to remove water, and results in enhanced shape retention by the starch moulds. After the mass has been deposited in the moulds, the moulds are stacked and transferred to drying ovens. The lozenges may be dried at any suitable temperature, for example 63-67° C., for approximately 30-34 hours. Preferably the final moisture content of the lozenges is approximately 10%.

Thus, a lozenge having a weight of approximately 2.25 g may have a final weight of approximately 1.50 g. Following drying, lozenges are bolted from the starch moulds, and starch is removed from the surface of the lozenges using air jets or brushes. The lozenges may then be coated with a glazing or anti-sticking agent such as Capol. This glazing provides a shiny or waxy finish to the lozenges, prevents sticking, and removes any residual starch attached to the lozenge surface.

The method of manufacture of the present lozenges is distinct from processes commonly used in manufacture of tablets, which are formed by compressing dry or granulated components.

According to a further aspect, the invention provides use of (i) a gum component and (ii) a non-crystallising sugar or non-crystallising sugar alcohol component in manufacture of a matrix for a buccal lozenge. The matrix is preferably glassy and non-crystalline in character. Any suitable gum component and non-crystallising sugar or non-crystallising sugar alcohol component can be used, for example, the components embodiment. The components can be used to manufacture a matrix by following steps (a) and (b) of the method of the second embodiment.

Generally, preferred lozenges of the invention containing water, gum acacia, non-crystallizing sorbitol, non-crystallising xylitol, non-crystallising maltitol, non-crystallising isomalt or other non-crystallizing sugar alcohol derivatives, homologues or associated sugars, and optional components such as phosphate buffers sodium or potassium hydroxide, and flavourings fall within the formula:—

| Excipient or Active Ingredient | Lozenge |
|---|---|
| Drug Substance | 0.01-200 mg |
| Acacia Spray Dried (anhydrous equivalent) | 600-1000 mg |
| Sorbitol, sugar alcohol, derivative or homologue | 200-500 mg |
| Non-crystallising Xylitol | 100-200 mg |
| Phosphate salt (1) | 0-50 mg |
| Phosphate salt (2) | 0-50 mg |
| pH adjuster | To desired pH |
| Water, Purified | 9-15% of total mass |
| Flavouring | 0-10 mg |
| Total | 1000-2000 |

The invention is now illustrated in the following non-limiting examples.

EXAMPLES

Example 1

Manufacture of Lozenges (General Procedures and Equipment)

Equipment

The following equipment items were used:

Dispensing scoops, sampling scoops, buckets and covers; batch mixing container; syrup pump; mass pump; jet cooker; holding tank; mixing tank; starch moulding machine; starch moulding trays; drying chamber; product trays and covers; polishing drum.

Initial Sampling

Sample 250 mL of purified water from the reservoir in the dispensing area. Send to laboratory for testing of *E. coli* and total viable aerobic count. Record the conductivity.

Preparation of Buffer Solution

In a tared bucket, dispense 30 kg of water, purified at 70° C. Add the buffers and dissolve and stir. Retain for the addition of buffer step.

Prepare a 30% Sodium hydroxide solution: In a tared bucket, dispense 14 kg of water, purified and carefully add the sodium hydroxide with constant stirring. When all the sodium hydroxide has dissolved, stir and retain for addition in later step.

Preparation of Nicotine Solutions

Prepare approximately 70% ethanol solution by mixing 14 liters of ethanol 96% with 6 liters of item water, purified.

For 1 mg—10% Nicotine Solution: Dispense the nicotine into a tared bucket. Add 5 kg of 70% ethanol solution mix and cover. Retain for addition in later step.

For 2 mg—10% Nicotine Solution: Dispense the nicotine into a tared bucket. Add 10 kg of 70% ethanol solution mix and cover. Retain for addition in later step.

For 4 mg—10% Nicotine Solution: Dispense the nicotine into a tared bucket. Add 20 kg of 70% ethanol solution mix and cover. Retain for addition in later step.

Preparation of Uncooked Mass

Dispense 276 kg of water, purified into the batch mixing container. Heat to 70° C. and thermostatically maintain the temperature. Add the sorbitol liquid (non-crystallizing), acacia (spray dried) and xylitol. Heat the pre-mix slurry with stirring for between 30 and 40 minutes maintaining a temperature of between 68° C. and 72° C.

Pump the mass to the holding tank. Run the pump until the batch mixing container is empty and complete the transfer with water.

Raise the temperature of the mass to between 70° C. and 74° C. and start the Jet Cooker. Pump the mass from the holding tank through the Jet cooker into the mixing tank, maintaining a temperature of between 113° C. and 117° C. and a vacuum of between −0.4 and −0.8 BAR. Continue the cooking process until all the mass has passed through the Jet Cooker into mixing container. Complete the transfer with water. Draw the last of the mass through the cooker into mixing tank by force of the vacuum. Maintain a cooking temperature of 113°-117° C.

Flavouring

For Classic Flavour—Allow the cooked mass to stand without stirring for approximately 20 minutes. Start the stirrer on slow speed and add 2.2 kg of Toffee Flavour QL17192.

For Citrus Flavour—Allow the cooked mass to stand without stirring for approximately 20 minutes. Start the stirrer on slow speed and add 2.1 kg of Orange Oil BP and 0.5 kg of Lemon Oil Ph.Eur.

For Spearmint Flavour—Allow the cooked mass to stand without stirring for approximately 20 minutes. Start the stirrer on slow speed and add 2.0 kg of Spearmint flavour.

Addition of Buffer and Nicotine

While continuing to stir add the buffer solution prepared in earlier step. Add 8.5 kg of 30% sodium hydroxide solution and if necessary, make further additions of 30% sodium hydroxide solution until a pH of 6.7 to 7.1 is obtained. While continuing to mix the mass, add the 10% nicotine solution completing the transfer with 1 liter of water, purified. Adjust the final batch weight to 1190.0 kg using water, purified. Close the tank and mix for 5 minutes. Maintain the temperature at between 68° C. and 70° C.

Moulding and Processing (Note: Moulding may be performed concurrently with batch formulation when using pre-conditioned starch.)

Preparation of moulding machine and moulds: Select the appropriate mould and dust with talc. Attach to the moulding machine. If using new moulding starch, fill mogul hopper with starch and operate the machine on recycle, filling and emptying the trays until 10 cycles have been completed. Add 25 kg of starch to the hopper after each cycle. If using pre-used (conditioned) moulding starch, fill the mogul hopper and present the pre-filled trays to the mogul for emptying, re-filling and stacking.

Allow the mass to rest for 20 minutes.

Set the moulding funnel temperature at 70° C. Pump the formulated mass from mixing tank into the moulding funnel of the mogul machine. After the transfer has been completed allow the formulated mass initially transferred to rest for 20 minutes. Start the moulding machine and deposit through the 48 mouthpieces into the starch moulds, adjusting the moulding weight to 2.25 g. The mogul tank is automatically kept at a constant fill level until the entire formulated product has been transferred from the mixing tank.

Operate the moulding machine at a rate of between 6 and 11 trays per minute until all the formulated mass has been deposited. Once moulding is complete, transfer the stacked trays to the drying chamber. Dry the lozenges at between 63° C. and 67° C. for between 30 and 34 hours. Record the temperature, time and drying atmosphere (% RH). Turn off the heating in the drying chamber and allow the lozenges to cool for 24 hours. The air temperature should drop to 30° C. before continuing. Return the trays to moulding machine. Bolt and sieve the lozenges from the starch collecting the lozenges in labelled product trays. Once full, cover the labelled trays with tray covers.

Finishing

Sample for chemical and microbiological testing. Transfer the lozenges to the sorting line, and remove any damaged or misshapen lozenges. Transfer the sorted lozenges to the polishing drum and apply Capol 4348 F at a rate of approximately 1 g per kilo of lozenges. (only about two thirds of the applied Capol 4348 F is deposited on the lozenges). During polishing sample every 30 minutes, bulking the samples. This sample is retained for use in Quality Control release testing. Record the weight and time for each sample taken. Pack the lozenges in labelled double wrapped polyethylene bags. Record the weight of each bag and dispatch the bulk packed lozenges to Inpac for packaging.

Packaging

Check the bulk container to confirm the identity of its contents. Assemble the lozenges, and pack seal and label them. During the packaging process "finished packed samples" are taken at regular intervals and a check lozenge-count is made.

Notes

If new moulding starch is used, complete the moulding prior to commencing batch formulation. To ensure the quality of the recycled starch, the total viable count test is performed prior to each moulding run.

Materials for Lozenges

Nicotine (Base) Ph Eur—Siegfried CMS, Zofingen Switzerland

Talc Powder Ph Eur—mfs

Toffee Flavouring QL17192—Quest International PO Box 2 1400 CA Bussum Holland

Tri-sodium Phosphate dodecahydrate extra pure E339—Merck KGaA, 64271 Darmstadt Germany Xylitol CX Ph Eur—Danisco Sweeteners, Redhill Surrey, UK C*Sorbidex NC 16205/7 (Sorbitol Non-crystallising Ph Eur)—Cerestar Krefeld Germany Instantgum AS—(Gum *Acacia* Ph Eur)—Colloides Natuerels International, Rouen, France Meritena 100—(Maize Starch to Ph Eur), Amylum Group, Vaexjoe, Sweden Capol 4348F—Kaul GMBH, Elmsholm Germany (polishing antisticking agent)

Ethanol 96% Ph Eur—Kemethyl, Haninge Sweden.

Sodium Dihydrogen Phosphate Dihydrate Ph Eur—Merck KGaA Darmstadt, Germany

Sodium Hydroxide Ph Eur—Merck KGaA Darmstadt, Germany

Lemon Oil Ph Eur

Orange Oil BP—R.C Treat and Co Ltd, Suffolk UK

Spearmint Flavour 79020—Givaudan, Dortmund Germany

Example 2

Lozenges were prepared using the method of Example 1, having the following constitution:—

Classic Flavour

| | | Formulation (kg) | | |
|---|---|---|---|---|
| Active Ingredient | Grade | 1 mg | 2 mg | 4 mg |
| Nicotine | Ph. Eur. | 0.53 | 1.06 | 2.12 |
| Excipients | | | | |
| Acacia, Spray-Dried | Ph. Eur. | 475 | 475 | 475 |
| Sorbitol, Liquid (Non Crystallizing) | Ph. Eur. | 253 | 253 | 253 |
| Xylitol | Ph. Eur. | 75.9 | 75.9 | 75.9 |

-continued

|  |  | Formulation (kg) | | |
|---|---|---|---|---|
| Active Ingredient | Grade | 1 mg | 2 mg | 4 mg |
| Sodium Dihydrogen Phosphate Dihydrate | Ph. Eur. | 16.0 | 16.0 | 16.0 |
| Tri-sodium Phosphate Dodecahydrate | In-House | 7.2 | 7.2 | 7.2 |
| Sodium Hydroxide | Ph. Eur. | 5.7 | 5.7 | 5.7 |
| Water, Purified | Ph. Eur. | 354.5 | 353.9 | 352.9 |
| Ethanol (96 Per Cent)* | Ph. Eur. | 3.5 | 7 | 14 |
| Toffee flavour QL17192 | In-House | 2.2 | 2.2 | 2.2 |
| Total weight (for 530,000 lozenges) |  | 1190 | 1190 | 1190 |

*= Evaporates during manufacturing process

Excipients not included in Lozenge formulation:—

|  |  | Formulation (kg) | | |
|---|---|---|---|---|
| Excipients | Grade | 1 mg | 2 mg | 4 mg |
| Talc** | Ph. Eur. | 0.1 | 0.1 | 0.1 |
| Maize Starch** | Ph. Eur. | 0.7 | 0.7 | 0.7 |
| Capol 4348 F** | In-House | 0.5 | 0.5 | 0.5 |

**= On surface only, not incorporated into lozenge

Example 3

Lozenges were prepared using the method of Example 1, having the following constitution:—
Citrus Flavour

|  |  | Formulation (kg) | | |
|---|---|---|---|---|
| Active Ingredient | Grade | 1 mg | 2 mg | 4 mg |
| Nicotine | Ph. Eur. | 0.53 | 1.06 | 2.12 |
| Excipients |  |  |  |  |
| Acacia, Spray-Dried | Ph. Eur. | 475 | 475 | 475 |
| Sorbitol, Liquid (Non Crystallising) | Ph. Eur. | 253 | 253 | 253 |
| Xylitol | Ph. Eur. | 75.9 | 75.9 | 75.9 |
| Sodium Dihydrogen Phosphate Dihydrate | Ph. Eur. | 16.0 | 16.0 | 16.0 |
| Tri-sodium Phosphate Dodecahydrate | In-House | 7.2 | 7.2 | 7.2 |
| Sodium Hydroxide | Ph. Eur. | 5.7 | 5.7 | 5.7 |
| Water, Purified | Ph. Eur. | 354.6 | 354.0 | 353.0 |
| Ethanol (96 Per Cent)* | Ph. Eur. | 3.5 | 7.0 | 14 |
| Orange Oil | BP | 2.1 | 2.1 | 2.1 |
| Lemon Oil | Ph. Eur. | 0.5 | 0.5 | 0.5 |
| Total weight (for 530,000 lozenges) |  | 1190 | 1190 | 1190 |

*= Evaporates during manufacturing process

Excipients not included in Lozenge formulation

|  |  | Formulation (kg) | | |
|---|---|---|---|---|
| Excipients | Grade | 1 mg | 2 mg | 4 mg |
| Talc** | Ph. Eur. | 0.1 | 0.1 | 0.1 |
| Maize Starch** | Ph. Eur. | 0.7 | 0.7 | 0.7 |
| Capol 4348 F** | In-House | 0.5 | 0.5 | 0.5 |

**= On surface only, not incorporated into lozenge

Example 4

Lozenges were prepared using the method of Example 1, having the following constitution:—
Spearmint Flavour

|  |  | Formulation (kg) | | |
|---|---|---|---|---|
| Active Ingredient | Grade | 1 mg | 2 mg | 4 mg |
| Nicotine | Ph. Eur. | 0.53 | 1.06 | 2.12 |
| Excipients |  |  |  |  |
| Acacia, Spray-Dried | Ph. Eur. | 475 | 475 | 475 |
| Sorbitol, Liquid (Non Crystallising) | Ph. Eur. | 253 | 253 | 253 |
| Xylitol | Ph. Eur. | 75.9 | 75.9 | 75.9 |
| Sodium Dihydrogen Phosphate Dihydrate | Ph. Eur. | 16.0 | 16.0 | 16.0 |
| Tri-sodium Phosphate Dodecahydrate | In-House | 7.2 | 7.2 | 7.2 |
| Sodium Hydroxide | Ph. Eur. | 5.7 | 5.7 | 5.7 |
| Water, Purified | Ph. Eur. | 354.7 | 354.1 | 353.1 |
| Ethanol (96 PerCent)* | Ph. Eur. | 3.5 | 7.0 | 14 |
| Spearmint flavour Nycomed 1043417 | In-House | 2.0 | 2.0 | 2.0 |
| Total weight (for 530,000 lozenges) |  | 1190 | 1190 | 1190 |

*= Evaporates during manufacturing process

Excipients not included in Lozenge formulation

|  |  | Formulation (kg) | | |
|---|---|---|---|---|
| Excipients | Grade | 1 mg | 2 mg | 4 mg |
| Talc** | Ph. Eur. | 0.1 | 0.1 | 0.1 |
| Maize Starch** | Ph. Eur. | 0.7 | 0.7 | 0.7 |
| Capol 4348 F** | In-House | 0.5 | 0.5 | 0.5 |

**= On surface only, not incorporated into lozenge

Example 5

Lozenges were prepared using the method of Example 1, substituting maltitol for sorbitol in lozenge B, having the following constitution:—
Toffee Flavour

| Excipient or Active Ingredient | Lozenge A | Lozenge B |
|---|---|---|
| Nicotine (mg) | 2.0 | 2.0 |
| Acacia Spray Dried (anhydrous equivalent) | 815.5+ | 800.5+ |
| Sorbitol or Maltitol Liquid (anhydrous Equivalent) | 334.9 (sorbitol) | 328.9 (maltitol) |
| Xylitol | 143.5 | 139.8 |
| Sodium dihydrogen phosphate (anhydrous equivalent) | 23.3 | 23.5 |
| Tri-sodium phosphate (anhydrous equivalent) | 5.9 | 6.0 |
| Sodium Hydroxide | 10.8 | 11.0 |
| Water, Purified | QS ~1500 | QS ~1500 |
| Ethanol 96% | 0 | 0 |
| Toffee Flavour QL17192 | 4.2 | 4.1 |
| Total | 1500 | 1500 |

+based on 9.2% water content used in pilot batch manufacture

All salts are given as anhydrous equivalents due to addition of water and drying of deposited lozenges.

Example 6

Measurement of pH in Lozenge

Measurement of pH of the lozenges made according to the invention, and also for comparison with known lozenges was undertaken by testing pH of a solution prepared by dissolving 1 g of finely divided lozenge in 20 mL of deionised water.

Example 7

Dissolution of Lozenges

Lozenges were prepared with the aim of providing a dissolution profile of, at 20 minutes=Mean of 35%-65%, at 40 minutes=Mean of 60%-90% and at 60 minutes=Mean greater than 70% and with the aim of providing stability of this profile over long term storage.

A first batch of lozenges were tested at 0 and 12 months after manufacture with the following results (the figures indicate percent dissolution):—

TABLE 1

| | Individual Data | | | | | Mean | | |
| --- | --- | --- | --- | --- | --- | --- | --- | --- |
| | 20 mins | 40 mins | 60 mins | | | 20 mins | 40 mins | 60 mins |
| Mean | 45.1 | 73.3 | 83.7 | 0 M | Mean | 45.1 | 73.3 | 83.7 |
| Min | 34.6 | 50.2 | 72.8 | | Min | 39.0 | 67.3 | 77.4 |
| Max | 64.9 | 91.6 | 91.6 | | Max | 60.1 | 87.4 | 88.9 |
| Mean | 42.2 | 72.1 | 87.3 | 12 M | Mean | 42.2 | 72.1 | 87.3 |
| Min | 34.4 | 60.0 | 77.7 | | Min | 37.4 | 62.4 | 81.8 |
| Max | 54.4 | 84.1 | 97.9 | | Max | 50.8 | 79.9 | 96.7 |

A second test was carried out on nicotine containing toffee flavoured lozenges, with the following results:—

TABLE 2

| Batch | Strength | 0 minutes | 20 minutes | 40 minutes | 60 minutes |
| --- | --- | --- | --- | --- | --- |
| 1A | 2 mg | 0 | 40 | 73 | 89 |
| 1B | 2 mg | 0 | 44 | 75 | 88 |
| 3A | 4 mg | 0 | 43 | 68 | 80 |
| 3B | 4 mg | 0 | 43 | 73 | 80 |

Dissolution was measured in pH 6.8 mixed phosphate buffer (5.76 g/Liter Disodium hydrogen orthophosphate, 2.29 g/liter Potassium dihydrogen orthophosphate, 1000 mL) using the Basket Method (Ph. Eur., 2.9.3, "Dissolution test for solid dosage forms") at 100 rpm.

Example 8

Lozenge Properties

Lozenges according to the invention were tested for stability and compared with lozenges of the invention of different formula and with known lozenges.

Stability of Active Ingredient

The long term stability of the active ingredient of the lozenge was tested, and the data are presented in Table 3. These demonstrate the enhanced stability characteristics of the lozenge. The introduction of a phosphate buffer system has been shown to complement chemical stability of the alkaloid nicotine. This is contrary to the incompatibility detailed in the literature, e.g. in the Handbook of Pharmaceutical Excipients. (Arthur H. Kibbe, Ph.D Pharmaceutical Press 2000)

TABLE 3

Long Term Assay Stability of Alkaloid (nicotine) containing Lozenges with Phosphate Buffer stored at 25° C./60% RH.

| Batch | Strength | 0 months | 3 months | 6 months | 9 months | 12 months | 18 months |
| --- | --- | --- | --- | --- | --- | --- | --- |
| 5A | 1 mg | 96 | 102 | 101 | 95 | 97 | — |
| 5B | 1 mg | 95 | 102 | 99 | 104 | 98 | — |
| 1A | 2 mg | 103 | 98 | 99 | 97 | 98 | 100 |
| 1B | 2 mg | 103 | 99 | 101 | 97 | 97 | 100 |
| 3A | 4 mg | 98 | 95 | 98 | 95 | 97 | 97 |
| 3B | 4 mg | 98 | 96 | 96 | 95 | 95 | 96 |

Comparative Data

The stability of 2 known nicotine-containing products were tested, and the data set out below.

TABLE 4

25° C./60% RH

| | Batch Number | 0 months | 3 months | 6 months |
| --- | --- | --- | --- | --- |
| Niquitin CQ Lozenge 2 mg | 031757 | 98.7% | 95.2% | 96.3% |
| Niquitin CQ Lozenge 2 mg | 032871 | 95.7% | 95.8% | 97.5% |
| Niquitin CQ Lozenge 4 mg | 032166 | 103.6% | 96.9% | 96.9% |
| Nicorette Gum 2 mg | 072546A | 97.1% | 104.0% | 103.1% |

TABLE 5

40° C./75% RH

| | Batch Number | 0 months | 3 months | 6 months |
| --- | --- | --- | --- | --- |
| Niquitin CQ Lozenge 2 mg | 031757 | 98.7% | 95.2% | 93.9% |
| Niquitin CQ Lozenge 2 mg | 032871 | 95.7% | 95.8% | 97.5% |
| Niquitin CQ Lozenge 4 mg | 032166 | 103.6% | 95.3% | 95.2% |
| Nicorette Gum 2 mg | 072546A | 97.1% | 93.8% | 100.3% | pH Stability

The pHs of aqueous solutions (5%) prepared from the lozenges buffered by phosphate salts were measured and it was found that these demonstrate excellent pH stability over extended periods of time. The results obtained are represented in Tables 6a and 6b. The data show better stability than for citrate buffering system presented in Tables 7a and 7b.

The phosphate buffers used were one or a combination of two or more of Sodium di-hydrogen phosphate, di-sodium hydrogen phosphate, potassium dihydrogen phosphate, di-potassium hydrogen phosphate, sodium hydroxide, potassium hydroxide, tri sodium phosphate and other alkali earth metal phosphate salts and hydrated salts thereof.

TABLE 6a pH stability of Alkaloid (nicotine) containing Lozenges with Phosphate Buffer stored at 25° C./60% RH.

| Batch | Strength | 0 months | 3 months | 6 months | 9 months | 12 months | 18 months |
|---|---|---|---|---|---|---|---|
| 5A | 1 mg | 8.1 | 8.0 | 8.2 | 8.0 | 8.3 | — |
| 5B | 1 mg | 8.2 | 8.1 | 8.2 | 8.1 | 8.5 | — |
| 1A | 2 mg | 8.0 | 8.2 | 8.0 | 8.0 | 8.0 | 8.2 |
| 1B | 2 mg | 8.4 | 8.5 | 8.0 | 8.5 | 8.5 | 8.3 |
| 3A | 4 mg | 8.3 | 8.2 | 8.0 | 8.1 | 8.4 | 8.1 |
| 3B | 4 mg | 8.4 | 8.4 | 8.4 | 8.3 | 8.5 | 8.4 |

TABLE 6b pH stability of Alkaloid (nicotine) containing Lozenges with Citrate Buffer stored at 25° C./60% RH.

| Batch | Strength | 0 months | 2 months | 3 months |
|---|---|---|---|---|
| LF6 | 2 mg | 7.1 | 6.9 | 6.7 |

TABLE 7a pH stability of Alkaloid (nicotine) containing Lozenges with Phosphate Buffer stored at 40° C./75% RH.

| Batch | Strength | 0 months | 1 months | 2 months | 3 months | 6 months |
|---|---|---|---|---|---|---|
| 5A | 1 mg | 8.1 | 8.0 | 8.1 | 8.0 | 8.0 |
| 5B | 1 mg | 8.2 | 8.2 | 7.9 | 8.0 | 8.1 |
| 1A | 2 mg | 8.0 | 8.2 | 8.3 | 8.2 | 8.0 |
| 1B | 2 mg | 8.4 | 8.6 | 8.3 | 8.5 | 8.2 |
| 3A | 4 mg | 8.3 | 8.4 | 8.2 | 8.2 | 8.0 |
| 3B | 4 mg | 8.4 | 8.5 | 8.3 | 8.4 | 8.2 |

TABLE 7b pH stability of Alkaloid (nicotine) containing Lozenges with Citrate Buffer stored at 40° C./75% RH

| Batch | Strength | 0 months | 1 month | 2 months | 3 months |
|---|---|---|---|---|---|
| LF6 | 2 mg | 7.1 | 6.7 | 6.5 | 6.2 |

Water Content

The moisture content of lozenges was evaluated during stability studies and the data obtained for moisture content for the phosphate buffered alkaloid (nicotine) lozenges and citrate buffered alkaloid lozenges are presented in Tables 8a and 8b.

Lozenges were prepared with the aim of a moisture content between 9 and 15% of total lozenge weight as determined by loss on drying after 24 hours at 105° C., this content to be stable during storage.

TABLE 8a

Water Content of Alkaloid (nicotine) containing Lozenges with Phosphate Buffer stored at 25° C./60% RH.

| Batch | Strength | 0 months | 3 months | 6 months | 9 months | 12 months | 18 months |
|---|---|---|---|---|---|---|---|
| 5A | 1 mg | 10.5% | 11.4% | 10.0% | 9.5% | 12.2% | — |
| 5B | 1 mg | 12.7% | 12.5% | 10.8% | 9.9% | 12.9% | — |
| 1A | 2 mg | 11.5% | 10.1% | 10.0% | 11.6% | 11.8% | 10.7% |
| 1B | 2 mg | 11.3% | 13.9% | 9.9% | 13.4% | 14.2% | 10.5% |
| 3A | 4 mg | 11.3% | 11.6% | 10.4% | 11.7% | 12.1% | 10.6% |
| 3B | 4 mg | 10.8% | 10.9% | 10.0% | 11.4% | 11.3% | 10.8% |

TABLE 8b

Water Content of Alkaloid (nicotine) containing Lozenges Manufactured with Citrate Buffer stored at 25° C./60% RH.

| Batch | Strength | 0 | 1 months | 3 months | 6 months | 9 months | 12 months |
|---|---|---|---|---|---|---|---|
| Prov 2 | 2 mg | 9.4% | 10.6% | 10.4% | 9.8% | 15.0% | 15.9% |
| Prov 4 | 2 mg | 12.9% | 13.7% | 12.8% | 12.2% | 16.0% | 16.1% |
| Prov 6 | 4 mg | 13.0% | 14.1% | 12.2% | 12.5% | 14.9% | 15.9% |
| Prov 8 | 4 mg | 14.7% | 14.6% | 11.7% | 14.5% | 14.0% | 15.9% |

Examples 9-14

Lozenges were prepared using a modified method of Example 1, in which the active agent was added to the formulation either as a micronised powder, or an ethanolic or aqueous solution. In Examples 9-11, in which the drug was ondansetron, the drug was added as a powder or an ethanolic solution. For Examples 12-14, in which the drug was sumatriptan succinate, the drug was added as a powder or an aqueous solution.

The lozenges were made with and without buffers to achieve physiological or stability-enhancing pH values for the matrix.

Example 9

Lozenges were prepared as described above, having the following constitution:—

| | |
|---|---|
| Ondansetron | 4 mg/8 mg (as hydrochloride) |
| Gum *Acacia* | 250 mg-400 mg |
| Xylitol | 50-200 mg |
| Sorbitol | 80-250 mg |
| Water | 40-80 mg |
| Flavour | 5-15 mg |
| Colour | 3-5 mg |

With or without Bitterness Reducing agent (0.1-20 mg)

Example 10

Lozenges were prepared as described above, having the following constitution:—

| | |
|---|---|
| Ondansetron | 4 mg/8 mg (as hydrochloride) |
| Gum *Acacia* | 250 mg-400 mg |
| Xylitol | 50-200 mg |
| Isomalt | 80-250 mg |
| Water | 40-80 mg |

-continued

| | |
|---|---|
| Flavour | 5-15 mg |
| Colour | 3-5 mg |

With or without Bitterness Reducing agent (0.1-20 mg)

Example 11

Lozenges were prepared as described above, having the following constitution:—

| | |
|---|---|
| Ondansetron | 4 mg/8 mg (as hydrochloride) |
| Gum *Acacia* | 250 mg-400 mg |
| Xylitol | 50-200 mg |
| Maltitol | 80-250 mg |
| Water | 40-80 mg |
| Flavour | 5-15 mg |
| Colour | 3-5 mg |

With or without Bitterness Reducing agent (0.1-20 mg)

Example 12

Lozenges were prepared as described above, having the following constitution:—

| | |
|---|---|
| Sumatriptan (as succinate) | 50 mg/100 mg |
| Gum *Acacia* | 300 mg-500 mg |
| Xylitol | 100-200 mg |
| Sorbitol | 100-300 mg |
| Water | 50-100 mg |
| Flavour | 5-15 mg |
| Colour | 3-5 mg |

With or without Bitterness Reducing agent (0.1-20 mg)

Example 13

Lozenges were prepared as described above, having the following Constitution:—

| | |
|---|---|
| Sumatriptan (as succinate) | 50 mg/100 mg |
| Gum *Acacia* | 300 mg-500 mg |
| Xylitol | 100-200 mg |
| Isomalt | 100-300 mg |
| Water | 50-100 mg |
| Flavour | 5-15 mg |
| Colour | 3-5 mg |

With or without Bitterness Reducing agent (0.1-20 mg)

Example 14

Lozenges were prepared as described above, having the following constitution:—

| | |
|---|---|
| Sumatriptan (as succinate) | 50 mg/100 mg |
| Gum *Acacia* | 300 mg-500 mg |
| Xylitol | 100-200 mg |
| Maltitol | 100-300 mg |
| Water | 50-100 mg |
| Flavour | 5-15 mg |
| Colour | 3-5 mg |

With or without Bitterness Reducing agent (0.1-20 mg)

The invention accordingly provides lozenges, and methods of manufacture thereof, for controlled buccal release and delivery of drugs.

The invention claimed is:

1. A glassy lozenge for buccal drug delivery comprising:
    a) a non-crystalline matrix having a hydrogel structure;
    b) an active agent selected from an anti-emetic agent, an agent for migraine treatment, and an analgesic agent;
    c) water; and
    d) optionally one or more components selected from flavorings, taste masking agents, colorings, buffering agents, pH adjusting agents, excipients, stabilizers and sweeteners,
    wherein the matrix comprises (i) at least one gum and (ii) at least one non-crystallising sugar or non-crystallising sugar alcohol; wherein the matrix comprises, by weight, from 40-90% of gum component (i), and from 60-10% of the non-crystallising sugar or non-crystallising sugar alcohol component (ii) and wherein the lozenge dissolves or disintegrates gradually.

2. A glassy lozenge according to claim 1, wherein the matrix comprises:
    i. at least one gum, and
    ii. at least one sugar and/or at least one sugar alcohol, wherein a major proportion of component (ii) consists of:
       A. one or more non-crystallising sugars,
       B. one or more non-crystallising sugar alcohols, or
       C. a mixture of one or more non-crystallising sugars and one or more non-crystallising sugar alcohols.

3. A glassy lozenge according to claim 2 wherein 50-90 wt % of component (ii) consists of:
    A. one or more non-crystallising sugars,
    B. one or more non-crystallising sugar alcohols, or
    C. a mixture of one or more non-crystallising sugars and one or more non-crystallising sugar alcohols.

4. A glassy lozenge according to claim 2 wherein 55-85 wt % of component (ii) consists of:
    A. one or more non-crystallising sugars,
    B. one or more non-crystallising sugar alcohols, or
    C. a mixture of one or more non-crystallising sugars and one or more non-crystallising sugar alcohols.

5. A glassy lozenge according to claim 2 wherein 60-80 wt % of component (ii) consists of:
    A. one or more non-crystallising sugars,
    B. one or more non-crystallising sugar alcohols, or
    C. a mixture of one or more non-crystallising sugars and one or more non-crystallising sugar alcohols.

6. A glassy lozenge according to claim 1 comprising (i) at least one gum, and (ii-a) at least one sugar and/or at least one sugar alcohol, wherein a major proportion of component (ii-a) consists of a non-crystallising mixture of sugars and/or sugar alcohols.

7. A glassy lozenge according to claim 6 wherein at least 50 wt % of component (ii-a) consists of a non-crystallising mixture of sugars and/or sugar alcohols.

8. A glassy lozenge according to claim 6 wherein at least 55 wt % of component (ii-a) consists of a non-crystallising mixture of sugars and/or sugar alcohols.

9. A glassy lozenge according to claim 6 wherein at least 60 wt % of component (ii-a) consists of a non-crystallising mixture of sugars and/or sugar alcohols.

10. A glassy lozenge according to claim 1 containing less than 10 wt % sucrose.

11. A glassy lozenge according to claim 10 containing less than 5 wt % sucrose.

12. A glassy lozenge according to claim 10 containing less than 2 wt % sucrose.

13. A glassy lozenge according to claim 10 containing less than 1 wt % sucrose.

14. A glassy lozenge according to claim 1, wherein the gum component (i) is selected from one or more of gum acacia, gum arabic, carob gum, carrageenan, ghatti gum, guar gum, karaya gum, pectin, tragacanth gum, locust bean gum, or xanthan gum.

15. A glassy lozenge according to claim 1, wherein the non-crystallising sugar or non-crystallising sugar alcohol component (ii) is selected from a non-crystallising form of any one or more of sorbitol, xylitol, maltitol, mannitol, and isomalt.

16. A glassy lozenge according to claim 15 wherein the non-crystallising sugar or non-crystallising sugar alcohol is a non-crystallising form of sorbitol, a non-crystallising xylitol or a mixture of non-crystallising sorbitol and non-crystallising xylitol.

17. A glassy lozenge according to claim 1 wherein at least 50% of component (ii) consists of a non-crystallising form of sorbitol.

18. A glassy lozenge according to claim 17 wherein at least 60% of component (ii) consists of a non-crystallising form of sorbitol.

19. A glassy lozenge according to claim 17 wherein at least 70% of component (ii) consists of a non-crystallising form of sorbitol.

20. A glassy lozenge according to claim 17 wherein at least 75% of component (ii) consists of a non-crystallising form of sorbitol.

21. A glassy lozenge according to claim 1 comprising approximately 5-20% by weight of water.

22. A glassy lozenge according to claim 1 comprising one or more buffering agents.

23. A glassy lozenge according to claim 22 comprising an alkali and a buffer salt.

24. A glassy lozenge according to claim 22, wherein the buffering agents comprise one or more phosphate salts.

25. A glassy lozenge according to claim 22 comprising at least one alkali metal phosphate salt as a buffering agent.

26. A glassy lozenge according to claim 25 wherein the alkali metal phosphate salts are selected from the group consisting of sodium dihydrogen phosphate and disodium hydrogen phosphate.

27. A glassy lozenge according to claim 22, wherein the buffering agents provides a final lozenge pH in the range 7.5-9.0.

28. A glassy lozenge according to claim 22, wherein the lozenge comprises a basic pH adjusting agent.

29. A glassy lozenge according to claim 1 having a dissolution profile such that
   after 20 minutes, 35-65% of the lozenge has dissolved;
   after 40 minutes, 60-90% of the lozenge has dissolved;
   and after 60 minutes, more than 70% of the lozenge has dissolved.

30. A glassy lozenge according to claim 1 wherein the active agent is a 5-HT agonist.

31. A glassy lozenge according to claim 1 wherein the active agent is a 5-HT antagonist.

32. A glassy lozenge according to claim 1 wherein the anti-emetic agent is ondansetron.

33. A glassy lozenge according to claim 1 wherein the agent for migraine treatment is sumatriptan.

34. A glassy lozenge according to claim 1 wherein the analgesic is A9-THC.

35. A glassy lozenge according to claim 1 comprising a sweetener, wherein the sweetener is a non-crystallising sugar, a non crystallising sugar alcohol, or a sugar or sugar alcohol treated so as to be non-crystallising.

36. A glassy lozenge for buccal drug delivery comprising an active agent selected from an anti-emetic agent, an agent for migraine treatment, and an analgesic agent, a non-crystalline matrix and a phosphate buffer, wherein the matrix comprises (i) a gum, and (ii) a non-crystallising sugar or non-crystallising sugar alcohol and wherein the matrix comprises, by weight, from 40-90% of gum component (i), and from 60-10% of the non-crystallising sugar or non-crystallising sugar alcohol component (ii).

37. A glassy lozenge according to claim 36 wherein the matrix comprises, not accounting for water, 55-62 parts acacia gum, 27-34 parts sorbitol, 7-11 parts xylitol and 1-13 parts Na phosphate.

38. A glassy lozenge according to claim 37 wherein the matrix comprises, not accounting for water, 56-58 parts acacia gum, 29-31 parts sorbitol, 8-10 parts xylitol and 1.5-2 parts Na phosphate.

39. A glassy lozenge according to claim 36 having a mass of 2 to 3 grams.

\* \* \* \* \*